United States Patent [19]
Maschke

[11] Patent Number: 5,835,558
[45] Date of Patent: Nov. 10, 1998

[54] MOBILE X-RAY EXPOSURE APPARATUS

[75] Inventor: Michael Maschke, Lonnerstadt, Germany

[73] Assignee: Siemens Aktiengesellschaft, Munich, Germany

[21] Appl. No.: 847,621

[22] Filed: Apr. 28, 1997

[30]   Foreign Application Priority Data

Jul. 9, 1996 [DE] Germany .......................... 196 27 657.8

[51] Int. Cl.[6] ...................................................... H05G 1/02
[52] U.S. Cl. ............................................ 378/198; 378/195
[58] Field of Search ..................... 378/198, 195

[56]   References Cited

U.S. PATENT DOCUMENTS

| 4,752,948 | 6/1988 | MacMahon . | |
| 5,327,474 | 7/1994 | Inoue et al. | 378/116 |
| 5,627,873 | 5/1997 | Hanover et al. | 378/198 |

FOREIGN PATENT DOCUMENTS

| 2645007 | 10/1990 | France . |
| 44 41 236 | 11/1993 | Germany . |

OTHER PUBLICATIONS

"Ein neuer fahbarer Röntgengenerator für den Einsatz in der Intensivstation; erste klinische Erfahrungen mit dem Mobilett," Lutz et al., Electromedica, vol. 4 (1982), pp. 116–119.

Die Entwicklung zur elektromobilen Röntgenbildverstärker–Fernseheinrichtung mit Grossflächenbildverstärker, Schöne, Rö.–Bl., Vo. 22 (1969), pp. 243–247.

"Flat (–Panel) Horizons in Digital X–Ray Imaging," Antonuk, Photonics Spectra, Jun. 1995, pp. 108–110, 112, 114 and 116.

Primary Examiner—Craig E. Church
Attorney, Agent, or Firm—Hill & Simpson

[57]   ABSTRACT

A portable x-ray exposure apparatus carries all components required for the production of an x-ray exposure. Two articulated arms are provided at a carriage, one carrying an x-ray source and the other carrying a flat detector that is formed by a matrix of detector elements. Image signals from the detector are supplied to image electronics in the carriage. The x-ray image generated by the image electronics is reproduced on a monitor or is transmitted to image data networks. The flat detector can be inserted under the patient in the bed.

4 Claims, 1 Drawing Sheet

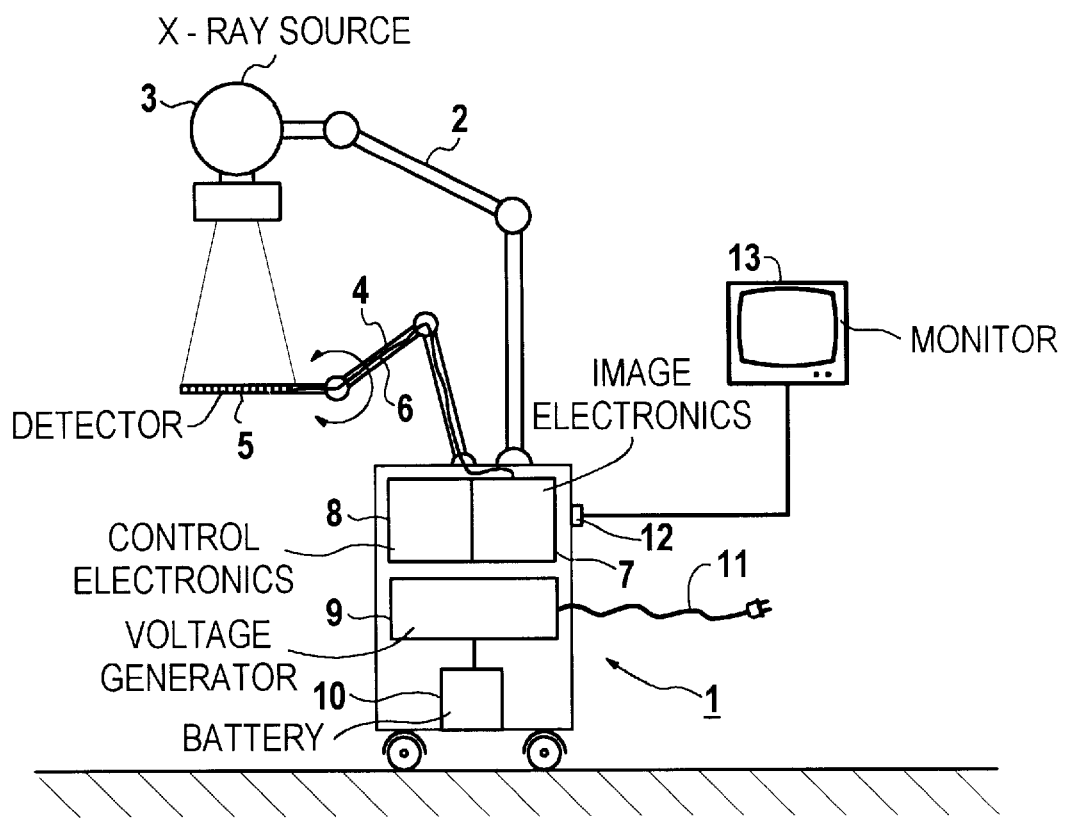

MOBILE X-RAY EXPOSURE APPARATUS

BACKGROUND OF THE INVENTION

1. Field of the Invention

The present invention is directed to a mobile x-ray exposure apparatus, of the type which can be moved adjacent the bed of a patient to obtain x-ray exposures of the patient in the bed.

2. Description of the Prior Art

It is known for producing x-ray exposures of a lying patient to insert an x-ray film cassette under the patient and to bring a carriage having a three-dimensionally adjustable x-ray source up to the patient bed. The x-radiator is then aligned such that the film in the x-ray film cassette is exactly struck by the x-rays (attenuated by the patient). The patient is lifted for the insertion and for the removal of the x-ray film cassette. The x-ray film cassette is thereby manipulated independently of the carriage supporting the x-ray source.

SUMMARY OF THE INVENTION

An object of the present invention is to provide an x-ray exposure apparatus which enables exposes of a lying patient and which carries all components required for an exposure.

This object is inventively achieved in an inventive x-ray exposure apparatus having a flat detector composed of a matrix of detector elements, preferably amorphous silicon (a-Si) detector elements, is provided, this being connected to the carriage (which also carries the x-ray source) by an articulated arm. Accordingly, the flat detector can be inserted under the patient at the patient bed as a consequence of its low structural height and an electronic image generation is possible. An additional advantage is the capability of structurally supported manipulation for inserting the detector under a patient.

DESCRIPTION OF THE DRAWING

The single figure is a side view of an exemplary embodiment of a mobile x-ray exposure apparatus, constructed in accordance with the principles of the present invention.

DESCRIPTION OF THE PREFERRED EMBODIMENTS

The drawing shows a carriage 1 displaceable on the floor that carries and supports an articulated arm 2 to which an x-ray source 3 is mounted so as to be threedimensionally adjustable in space. A second articulation arm 4 carriers a flat detector 5, likewise three-dimensionally adjustable in space. The flat detector 5 is formed by a matrix of detector elements, preferably the amorphous silicon detector elements. The detector signals from the detector elements are supplied to image electronics 7 via a line 6 guided in the articulated arm 4. Control electronics 8 serves for controlling readout at the flat detector 5 as well as controlling a voltage generator 9 arranged in the carriage 1. The voltage generator 9 is supplied by a battery 10 that can also be formed by an accumulator that can be charged via a mains connection 11.

The output image signals of the image electronics 7 can be supplied via a plug-type connection 12 to a monitor 13 and/or to image data networks for image playback. monitor for image playback, however, can also be directly attached to the carriage 1.

For production of an x-ray exposure at a sick bed, the illustrated x-ray exposure apparatus is moved up to the bed, the flat detector 5 is inserted under the bed or under the patient, and the x-radiator 3 is set such that the flat detector 5 is fully struck by the x-ray beam.

The illustrated x-ray exposure apparatus also allows exposures of a standing or sitting patient. To this end, the flat detector 5 can be correspondingly adjusted. For an exposure of the standing patient, the detector 5 is pivoted into a vertical position, with the position of the x-ray source 3 being correspondingly set. The battery 10 can also be eliminated when the x-ray generator 9 is directly connected to the mains terminal 11.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mobile x-ray exposure apparatus comprising:
   a manually movable portable carriage having non-motorized means for freely moving said carriage without any directional constraint;
   an x-ray source and first articulation means attached to said portable carriage for mounting said x-ray source on said portable carriage for allowing three-dimensional position adjustment of said x-ray source;
   a flat radiation detector comprised of a matrix of detector elements which emit image signals dependent on radiation from said x-ray source incident thereon;
   second articulation means attached to said portable carriage separately form said first articulation means, for mounting said flat detector on said portable carriage for allowing three-dimensional position adjustment of said flat detector; and
   image electronics, completely contained in said portable carriage, supplied with said image signals and emitting video signals, at an output within said portable carriage, produced from said image signals.

2. An x-ray exposure apparatus as claimed in claim 1 further comprising a plug on an exterior of said portable carriage connected to said output of said image electronics for supplying said video signals to a playback arrangement selected from the group consisting of a video monitor and an image data network.

3. An x-ray exposure apparatus as claimed in claim 1 further comprising a voltage generator completely contained in said portable carriage and connected to said x-ray source, said voltage generator having a mains terminal, proceeding from said portable carriage connectable to an external power source for supplying power to said voltage generator.

4. A mobile x-ray apparatus as claimed in claim 1 further comprising a voltage generator contained in said carriage and connected to said x-ray source, and a battery contained in said carriage and connected to said voltage generator for supplying power to said voltage generator, said battery having a mains terminal connectable to an external power source for recharging said battery.

* * * * *